United States Patent [19]

Kaye

[11] Patent Number: 5,292,483
[45] Date of Patent: Mar. 8, 1994

[54] DETECTING A RADIATION SIGNAL

[75] Inventor: Wilbur I. Kaye, Princeville, Hi.

[73] Assignee: Beckman Instruments, Inc., Fullerton, Calif.

[21] Appl. No.: 938,818

[22] Filed: Sep. 1, 1992

Related U.S. Application Data

[63] Continuation-in-part of Ser. No. 722,823, Oct. 8, 1991.

[51] Int. Cl.$^5$ .................. G01J 1/58; G01N 21/49; G01N 21/85

[52] U.S. Cl. .................. 422/82; 250/458.1; 356/246; 422/82.05; 436/164; 436/172

[58] Field of Search .................. 422/822, 82.05, 82.11, 422/82.08; 356/246, 317, 417; 250/458.1, 459.1, 461.1; 436/164, 172

[56] References Cited

U.S. PATENT DOCUMENTS

| | | | |
|---|---|---|---|
| 3,795,450 | 3/1974 | Munk | 356/246 |
| 4,088,407 | 5/1978 | Schoeffel et al. | 356/246 |
| 4,172,227 | 10/1979 | Tyrer et al. | 250/461.1 |
| 4,199,686 | 4/1980 | Brunsting et al. | 356/342 |
| 4,273,443 | 6/1981 | Hogg | 356/343 |
| 4,367,040 | 4/1983 | Goto | 356/44 |
| 4,565,448 | 1/1981 | Abbott et al. | 356/246 |
| 4,657,397 | 4/1987 | Oehler et al. | 356/414 |
| 4,675,300 | 6/1987 | Zare et al. | 436/172 |
| 4,786,171 | 11/1988 | Le Febre et al. | 356/246 |
| 4,801,552 | 1/1989 | Hoff | 436/173 |
| 4,927,265 | 5/1990 | Brownlee | 356/73 |
| 4,929,561 | 5/1990 | Hirschfeld | 436/116 |
| 4,997,275 | 3/1991 | Gaucher et al. | 356/246 |
| 5,062,942 | 11/1991 | Kambara et al. | 204/299 |
| 5,108,179 | 4/1992 | Myers | 356/344 |

FOREIGN PATENT DOCUMENTS

| | | |
|---|---|---|
| 0404646 | 12/1990 | European Pat. Off. |
| 153248 | 3/1981 | Japan . |
| 147840 | 11/1988 | Japan . |
| 147841 | 11/1988 | Japan . |
| 330564 | 9/1990 | Japan . |
| 1128361 | 9/1968 | United Kingdom . |
| 2155176A | 9/1985 | United Kingdom . |

OTHER PUBLICATIONS

"High-Sensitivity Fluorescence Detector . . . ", Shaole Wu and Norman J. Dovichi, Journal of Chromatography, 480 (1989) 141-155.

"Electrokinetic Resolution of Amino Acid Enantiomers . . . ", Philippe Gozel, Ernst Gassmann, Hope Michelson, Richard N. Zare, Anal. Chem., 1987, 59, 44-49.

"On-Line Connector for Microcolumns . . . ", Stephen L. Pentoney, Jr. Xiaohua Huang, Dean S. Burgi, Richard N. Zare, Anal. Chem., 988, 60, 2625-2629.

"Laser Induced Fluorescence Detection . . . ", Staffan Folestad, Lar Johnson, Björn Josefsson, Anal. Chem., 1982, 54, 925-929.

"Small-Bore LC/Laser Fluorescence", Staffan Folestad, Bo Galle, Björn, Journal of Chromatographic Science, vol. 23, Jun. 1985.

"Simultaneous Laser-Based Refractive Index . . . ", Darryl J. Bornhop, Norman J. Dovichi, Anal. Chem., 1987, 59, 1632-1636.

"Fluorescence-activated Cell Sorting", Leonard A. Herzenberg, Richard G. Sweet, Leonore A. Herzenberg, Scientific American, 234, No. 3, 108-117.

"Fluorescence Detection in Capillary Zone Electrophoresis . . . ", J. V. Sweedler, J. B. Shear, H. A. Fishman, R. N. Zare, reprinted from Anal. Chem., 1991, 63, 496-502.

"Analytical Biotechnology, Capillary Electrophoresis and Chromatography", ACS Symposium Series 434, Sep. 25 ∝ 30, 1988 (booklet).

*Primary Examiner*—James C. Housel
*Assistant Examiner*—Ramon Torres
*Attorney, Agent, or Firm*—William H. May; Gary T. Hampson; Charles Berman

[57] ABSTRACT

Focusing a generated radiation signal on a detector is effected by a curvilinear surface. The radiation beam signal from the reflected surface is collimated or focused on the detector. Light scattered, Raman scattered, fluorescence, chemiluminescence, phosphorescence radiation signals from particles as a result of a chemical procedure or reaction is enhanced through this focusing technique. The enhanced signal which is detected is subsequently measured through different detection techniques.

52 Claims, 7 Drawing Sheets

DETECTING A RADIATION SIGNAL

RELATED APPLICATION

This application is a continuation-in-part of the co-pending application Ser. No. 07/772,823 filed Oct. 8, 1991 and entitled "Enhanced Fluorescence Detection of Samples in Capillary Column." The contents thereof are incorporated by reference.

BACKGROUND

This invention relates to the efficient collection and detection of low levels of radiation arising within microliter volumes of sample.

The radiation may be in the form of luminescence from a chemical reaction or result from the interaction of an intense light source and the sample. Alternatively, the processes of light scattering, Raman scattering, fluorescence and phosphorescence may be used.

The technique of light scattering is particularly useful in the detection of particles, and two broad classifications of instruments can be identified. Particles of diameters significantly smaller than the wavelength of probe light scatter isotropically, i.e. equally in all directions. This type of scattering is usually called Rayleigh scattering. Particles of diameters significantly larger than the wavelength of probe light scatter primarily in the forward direction and, often, the intensity of scatter is a complicated function of scattering angle. This type of scattering is usually called Mie scattering. The intensity of forward scattered light varies as the sixth power of the particle diameter; hence, special precautions must be taken when attempting to measure the light scattered from very small particles.

The present invention permits for the determination of relative particle size and/or concentration of very small particles, particularly in a flowing system.

Intense light sources such as lasers are used for studying small particles. The use of such sources introduces problems associated with discrimination of light scattered by instrumental components from that scattered by the sample. The intensity of light scattered from small particles may be less than one millionth the intensity of laser radiation. To measure such low intensities, it is necessary to collect as much of the light scattered by the sample as possible, yet reject that scattered by the instrument. In general, it becomes increasingly difficult to eliminate instrumental light scattering as the angle of detected scattering decreases. Consequently, when measuring the light scattered by particles significantly smaller than the wavelength of probe light, it is best to avoid detection of the small angle scattering, while collecting as large a solid angle of scattered light as possible.

When measuring the light scattered by small particles, considerable attention must be paid to the overwhelming level of light scattered from unwanted foreign particles of large size. For this reason, it is advantageous to keep the size of the scattering volume (volume of sample simultaneously illuminated and detected) as small as possible. In a flowing sample, these particles will be evidenced as signal "spikes" abruptly rising from a base signal. The base signal represents the signal from the more numerous small particles.

Large angle scattered light instruments described in the prior art have used large scattering volumes and require extensive sample treatment to minimize the detection of large foreign particles. Furthermore, sample volume has to be large to avoid detection of light scattered from the instrument. These prior art instruments have usually used lenses and apertures to define the scattering angle and, of necessity, capture a small solid angle of scattered light.

Moreover, most of the prior art has addressed the detection of relative large biological cells (cytometry). The signals from these large particles are much greater than those provided by the small particles of particular interest in the present invention.

Raman scattering is used for the chemical characterization of the samples rather than particle size. Like Rayleigh scattering, the signal intensities are very low and it is important to capture as large a solid angle of Raman scattered light as possible while also using very intense sources of incident radiation. The Raman scattered signals are of different wavelength from the incident light. Chemical characterization of the sample is determined by the difference between the frequency of the Raman signal and the frequency of the exciting radiation. It is customary to use a blocking filter to reject the incident radiation followed by a monochromator to determine the frequency of the Raman signal. While this frequency difference helps in the discrimination between exciting and Raman signals, the Raman bands are often narrow; hence, the signals are very weak. It is important to use whatever geometric means are available to minimize the detection of the incident radiation and maximize the detection of the weak Raman radiation from the sample.

Fluorescence techniques are used when the sample or some component(s) of the sample can be tagged with a fluorescing dye. The sample is then excited by an intense beam of exciting radiation, usually from a laser. The wavelength of the exciting radiation is chosen to correspond to the wavelength of maximum sample excitation. The wavelength of the fluorescing radiation will usually be greater than the exciting wavelength, and a filter or monochromator will be chosen to pass only that radiation corresponding to the wavelength of maximum fluorescence emission. When the sample concentration is low, great care is needed in the choice of filters or monochromators in order to discriminate between exciting and fluorescing wavelengths. No filters provide a perfect discrimination, and it is desirable to use whatever geometric means are available to minimize the detection of exciting rays scattering from the instrument. Under ideal conditions, tagged molecules can be detected at extremely low concentration.

Phosphorescence techniques are employed where the sample, itself, or the tagged sample continues to emit radiation a significant time after excitation. Time as well as wavelength can then be used to discriminate between exciting and emitting radiation.

Luminescence techniques are used when the sample or some component of the sample emits radiation as a result of a chemical reaction of the sample with a reagent. No external exciting radiation is needed; hence, all of the radiated light may be detected without recourse to filtering. However, the luminescence signals are usually very weak and depend on the number of reacting molecules within the detected sample volume. A compromise must usually be made between detected sample volume and concentration of reacting molecules. The efficient collection and detection of the radiation emitted within the detected sample volume is of great importance.

There is a need to provide a system for radiation collection and detection which provides significant advances over the prior art.

SUMMARY

By this invention, there is provided a system for detecting a radiation signal in a manner which minimizes disadvantages of the prior art.

According to the invention, a generated radiation signal from an excited sample is collected over a large solid angle by means of a reflecting curvilinear surface of revolution and is directed to a detector. The angle should preferably be between about 35° and 145°.

The sample enters a detection volume in a flowing stream and the axis of sample flow is collinear with the axis of revolution of the reflecting curvilinear surface of revolution. The scattering volume, which is part of the detection volume, is retained relatively small.

In one preferred form, the radiation signal after the above interaction has the same wavelength as the radiation signal incident on the sample. This type of interaction is called "light scattering." The incident radiation is of high intensity and is usually produced by a laser. There are means for directing this laser beam along an axis of the curvilinear reflection means.

In particular, small volumes of sample flow past the point of interaction. The axis of sample flow is coaxial with the axis of a reflective light collector. There are also means for directing a sample flow in a tube along an axis collinear with the laser beam in such a way that the beam impacts the sample without impacting the sample tube wall. In this manner, the three axes are collinear.

The scattered light ray output is the generated signal at the focus of the reflecting means.

The output reflection signal from the reflective means can be a collimated beam which is directed to a detector directly. The reflecting curvilinear surface of revolution producing a collimated beam is selectively a paraboloid. The collimated beam may also be focused onto a detector by a focusing lens. Alternatively, the curvilinear means can reflect the generated signal directly to a remote focal point. The curvilinear means for doing this is preferably an ellipsoid.

In different forms of the invention, the generated radiation signal may arise selectively from light scattering, Raman scattering, fluorescence, phosphorescence or luminescence.

The invention is further described with reference to the accompanying drawings.

DESCRIPTION

Figure 1:
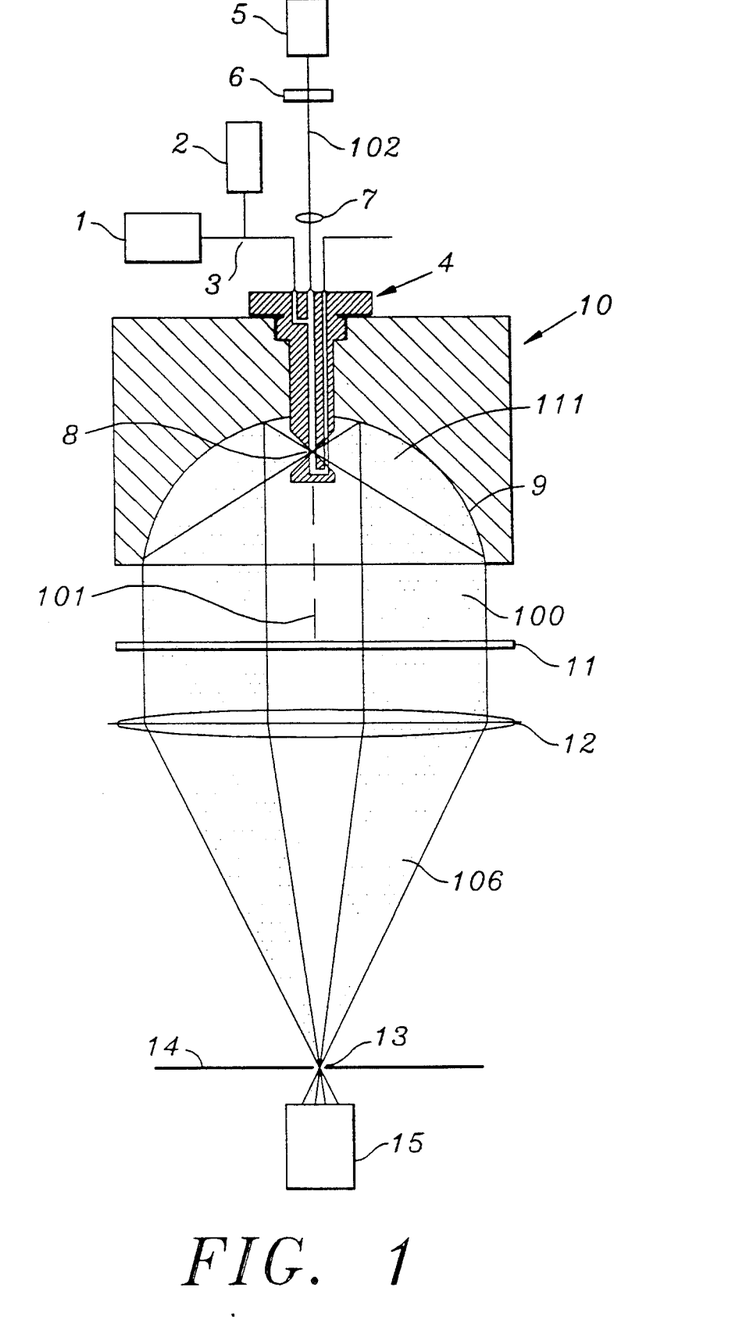
FIG. 1 shows the invention used to monitor some property of a sample as it changes in time as a result of passage through a separation means. The sample may be mixed with a reagent, and the geometric axes in the vicinity of the point of radiation generation are illustrated.

FIG. 1 identifies the major components of the system. A sample processed by some type of separation system 1, such as a chromatograph column, mixes with a reagent from a delivery system 2 at point 3. The mixture enters a sample containment vessel 4. An intense light source 5 such as a laser produces a beam 102 which is filtered by a filter 6 and focused by a lens 7 onto a point of radiation generation 8. This generation point 8 corresponds to a focal point of a curvilinear surface of revolution 9 milled into a block 10.

In this illustration, the curvilinear surface 9 is a paraboloid. The surface 9 of this paraboloid is reflecting and collimates the radiation generated at the point 8. From the point 8, there is generated a beam 111 of incident radiation which is directed through a large solid angle to reflective surface 9. The collimated beam 100 of reflected radiation is filtered by a filter 11 and focused by a lens 12 onto an aperture 13 in a plate 14. Radiation passing through the aperture 13 is detected by a detector 15.

An imaginary straight line 101 from the intense light source 5 to the aperture 13 defines the axis of the curvilinear surface 9 and also the axis of sample flow in the vicinity of the point of generation 8. Where pertinent, this imaginary line 101 defines the axis of the exciting light beam 102 in the vicinity of the point 8 of radiation generation.

Figure 2A:
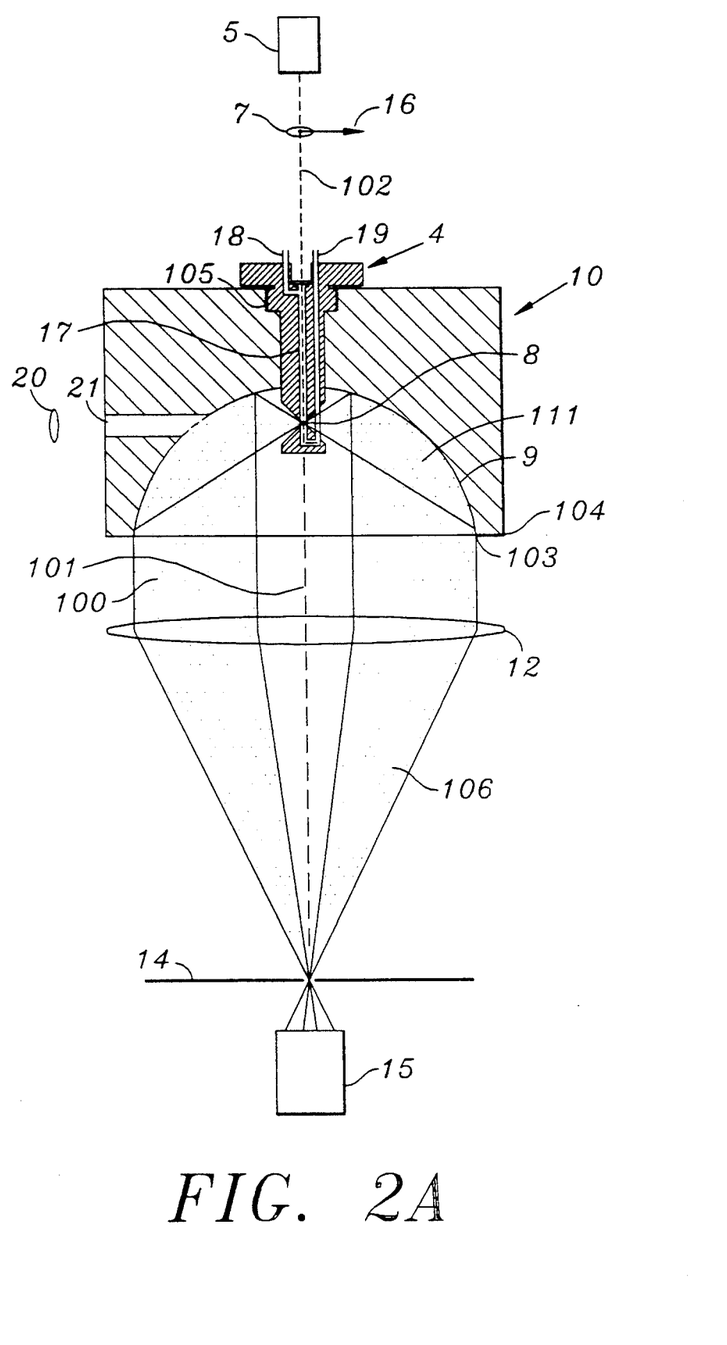
FIGS. 2A and 2B are respectively a side diagrammatic view and end diagrammatic view of the system for detection of scattered light.

FIG. 2A shows an embodiment of the invention specifically for the detection of scattered light. The light beam 102 from a laser 5 is focused by the lens 7 and directed by means of a two-axis adjusting device 16 down the axis of a channel 17 in the sample containment vessel 4 which screws into the block 10 of the paraboloid. The sample from point 3 enters the containment vessel 4 at 18 and exits at 19.

The laser beam 102 must not strike the walls of the channel 17 in the sample containment vessel 4. Alignment is accomplished by viewing the generation point 8 by means of viewing lens 20 and a hole 21 in block 10 into which the curvilinear surface 9 is formed.

The lens 12 and the aperture in plate 14 serve as a spatial filter and allow only the radiation generated at 8 from passing to the detector 15. In some applications, this spatial filter is unnecessary, but the photosensitive area of the detector 15 must then be as large as the mouth of the paraboloid.

Figure 2B:
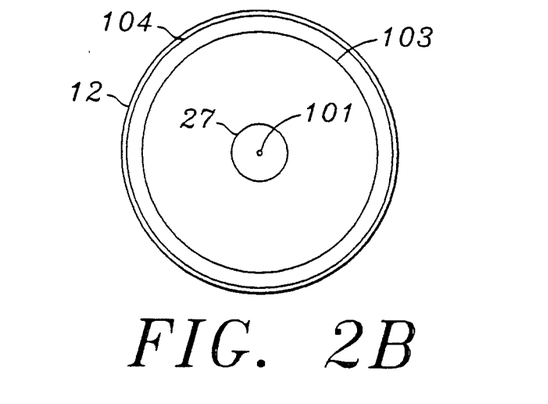

FIG. 2B is an end view of the apparatus looking down the axis of revolution 101 of the curvilinear surface 9. Looking into the open of the paraboloid, one "sees" the end of the end cap 27 of the containment vessel. The inner edge 103 and outer edge 104 of the paraboloid mouth as well as the outer edge of the lens 12 are visible.

Figure 3:
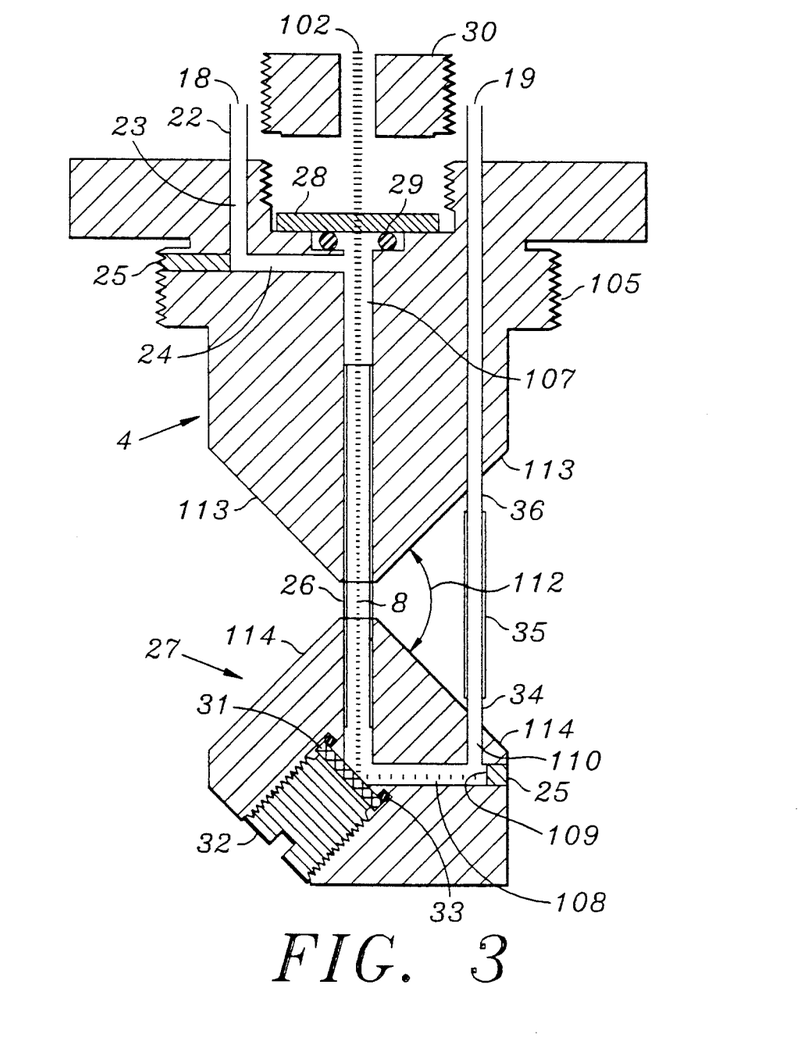
FIG. 3 shows the details of the containment vessel insert fitting into the curvilinear reflecting surface.

FIG. 3 shows the details of the sample containment vessel 4 and the end cap 27. The parts are made of a material such as black "Delrin." The containment vessel 4 is threaded at 105 to fit into the paraboloid block 10 which has mating threads and position the generation point 8 at the focal point of the paraboloid surface 9.

The sample enters at 18 through a stainless steel tube 22 tightly inserted in a hole 23 drilled into the black plastic. At a point below the stainless steel tube 22, a second hole 24, at 90° to the first hole 23, is drilled into the black plastic and conveys the sample mixture to channel 107 running down the axis of the containment vessel. The second hole 24 is closed by plug 25 to keep the sample mixture from escaping from the desired channel 24. A glass tube 26 fits tightly into bore 107 in the sample containment vessel 4 and extends into the second black plastic end cap 27.

A glass plate 28 serves as a window to allow laser radiation 102 to pass into the containment vessel while keeping the sample in its channel 24. The glass plate 28 is held against an "O ring" 29 by means of retainer 30. The glass tube 26 does not come in optical contact with the glass plate 28. Thereby, the light scattered at the sur-face of the glass plate 28 does not channel into the glass tube 26. Were a significant fraction of the light scattered by glass plate 28 to enter tube 26, some unwanted radiation could escape from tube 26 in the vicinity of the generation point 8.

The end cap 27 allows the sample to exit the system through hole 108 and also acts as a light trap for the excess incident radiation from laser beam 102. A plate 31 of polished black glass acts as the primary light trap. This plate 31 is angled to send the weak reflected beam to the end wall 109 at the end of hole 108. The black glass plate fits against the wall of the black plastic by means of a threaded plug 32. Another "O-ring" 33 seals against escape of the sample stream. A second plug 25 again confines the sample to the desired stream.

A short piece of stainless steel tubing 34 fitted into a hole 110 conveys the sample stream to a piece of Teflon (Polytetrafluoroethylene) tubing 35 which mates with still another piece 36 of stainless steel tubing by which the sample stream exits the containment vessel at 19. The plastic tubing 35 blocks only a negligible portion of the scattered rays from falling on the paraboloid.

The end cap 27 is dimensioned to slip through the hole in the paraboloid block 10 at its base.

The solid angle 112 of incident radiation is between about 45° and 135° relative to the axis 101. The end face 113 of the vessel 4 defines one limit of the angle 112. The end face 114 of the end cap 27 can define a second limit of the angle 112. Faces 113 and/or 114 form occlusion means about the tube defining radiating barrier means relative to the local point to define the solid angle. Alternatively to the end face 114, the limit 103 of the parabaloid surface 9 can limit the extent of the angle, as illustrated in FIGS. 1 and 2A and 2B.

Figure 4:
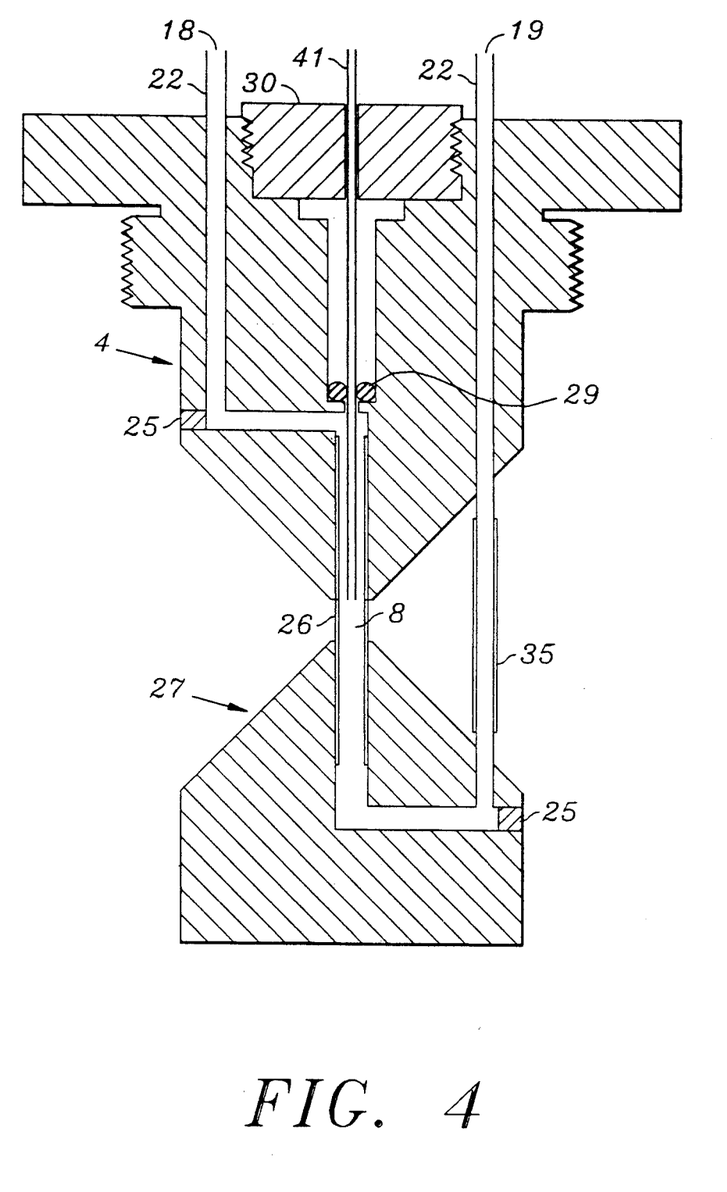
FIG. 4 shows an alternate design of the insert in a configuration optimized for the detection of sample luminescence.

FIG. 4 shows another embodiment of the containment vessel 4 and its end cap 27. In this case, the sample mixture is introduced to the generation point by means of a capillary tubing 41. A chemiluminescence reagent is introduced through entry 18. This embodiment is primarily intended for use with chemiluminescent samples. Exciting light source is not necessary in this application. It is presumed that the luminescence resulting from the chemical reaction is of short lifetime, hence, has a maximum intensity at the point of reaction which in this case occurs at the generation point.

Figure 5:
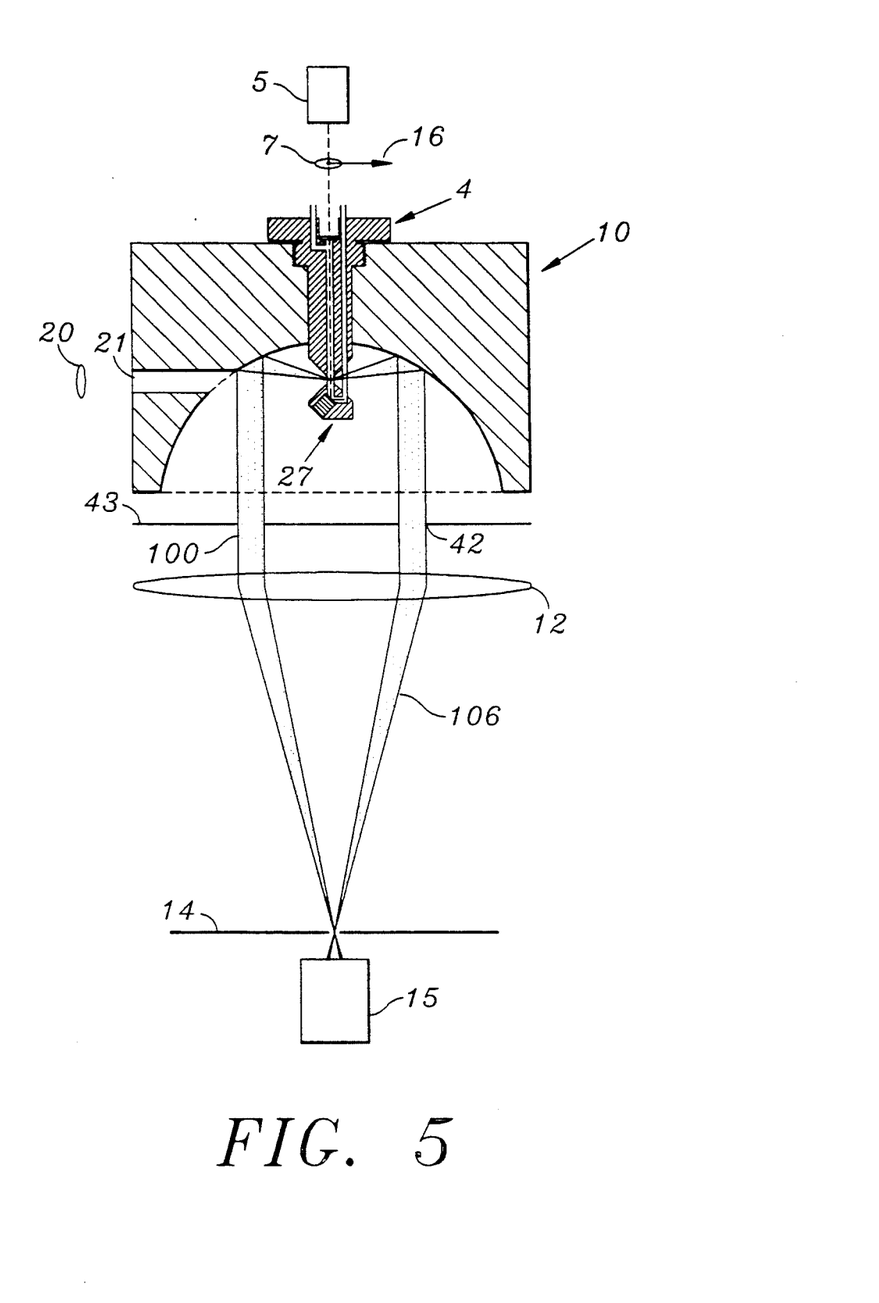
FIG. 5 is a diagrammatic view of an embodiment wherein an annular aperture determines the detected scattering angle of a scattering signal.

FIG. 5 is similar to FIG. 2A and is useful in certain types of light scattering measurements. Plate 43 with an annular aperture 42 is inserted into the apparatus where the beam from the sample is collimated. The inner and outer diameters of this annular aperture determine the solid angle 112 of detected scattered light.

Figure 6:
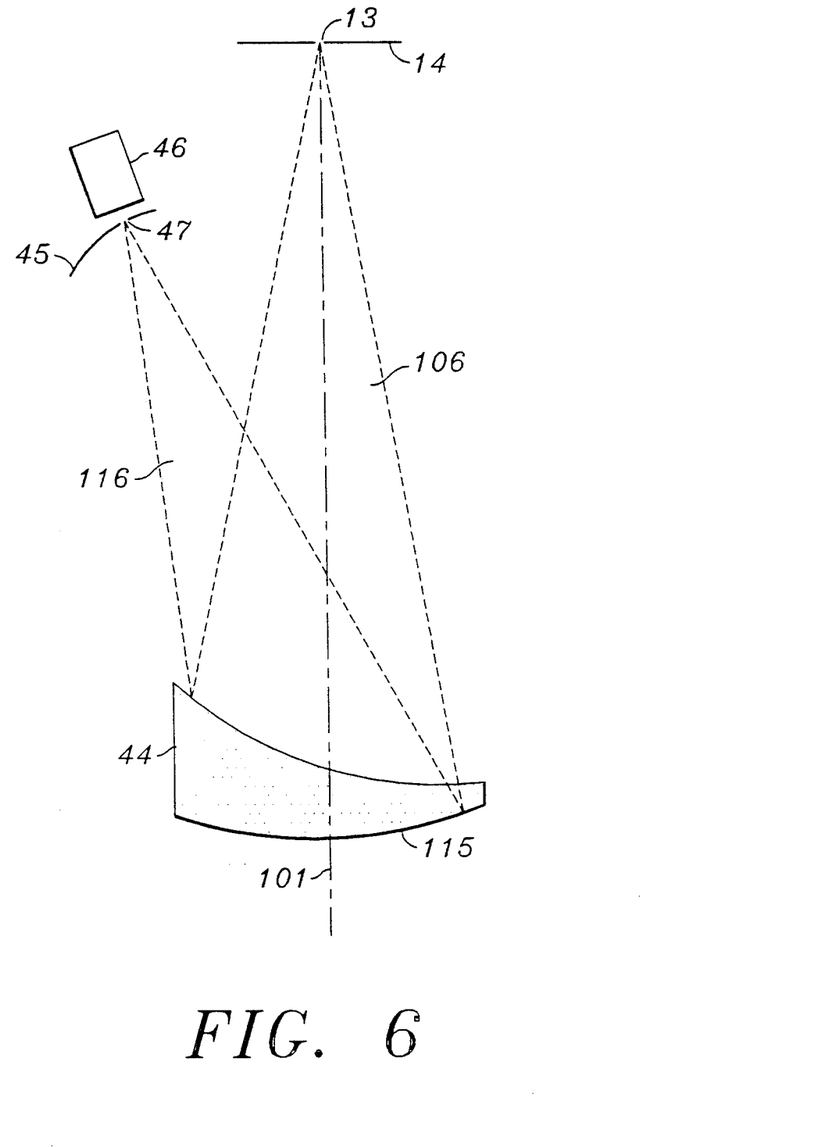
FIG. 6 is a diagrammatic view of a monochromator suitable for addition to any of the above light collection systems. A Fery prism is used to disperse the radiation onto one or more detectors. An aperture plate in the focal surface and in front of the detector(s) determines the portion of the spectrum detected. Alternatively, an array detector may be located at the focal surface of the prism and the spectrum measured.

FIG. 6 is an extension of FIG. 2A and shows the focused radiation 106 passing through the aperture 13 in plate 14 and on to a Fery prism 44 which disperses the radiation 116 and focuses a spectrum on a curved plate 45. The location and size of the aperture 47 in plate 45 determines the wavelength and wavelength interval of radiation detected by detector 46. A multiplicity of apertures and detectors may be used when it is desired to monitor different spectral intervals simultaneously. Similarly, means other than a Fery prism may be used to disperse radiation 106.

Alternately, an array detector may be positioned in place of the aperture plate. The signal from the array of detectors 46 may be processed in the usual manner to provide the dynamic changing spectra as samples flow through the system. It should be apparent that any type of dispersing system may be employed in FIG. 6. However, the Fery prism 44 affords a high efficiency along with low stray light.

Figure 7:
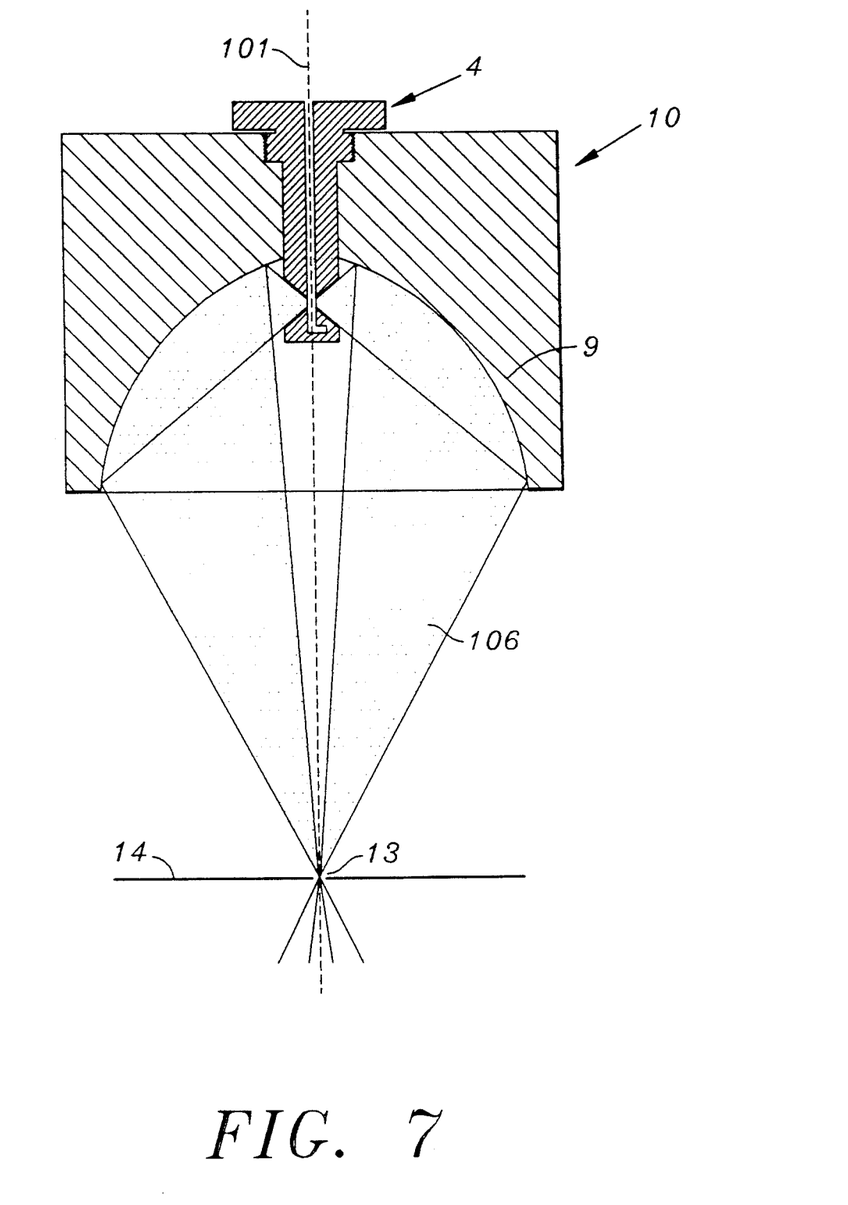
FIG. 7 is an embodiment illustrating an ellipsoidal version of the reflective surface, and is similar to FIGS. 2A and 2B.

When there is no need to filter the light from the sample (by means of filter 111 shown in FIG. 1), surface 9 of block 10 may be in the shape of an ellipsoid. As shown in FIG. 7, the beam 106 is then focused directly onto aperture plate 14 and lens 12 is not needed.

Applications

Description of a few applications for the above equipment may help to understand the invention.

The apparatus in its light scattering configuration is useful in the study of antigen-antibody reactions. When the antigen specific to an antibody mixes with a solution containing the antibody, there is a reaction producing aggregates of rapidly increasing size. If the concentration of antibody and antigens is sufficiently high, the aggregates may become large enough to see with the naked eye. However, at low concentration, the limiting aggregate size may be submicroscopic and detectable only by very sensitive light scattering techniques.

The above invention is applicable to the screening of antibody-antigen reactions wherein a separation technique isolates fractions of either antibodies or antigens. As the components elute from the separations means 1 and mix with a potential conjugate steadily flowing from 2, the sample generates an elevated scattered light signal, indicative of an aggregating pair. The detector means 15 can be set up to respond to a spatial or temporal signal from the generating point 8.

Raman spectra often characterize particular classes of molecular structure. A detector can sense when sample fractions having that particular class of structure elute from a chromatograph column 11.

Fluorescence and phosphorescence techniques provide for extremely sensitive detection of classes of samples eluting from a separation system when certain classes of effluent can be tagged with a fluorescent dye or set of dyes. For example, DNA fragments of different size may be chromatographed to separate fragments by molecular weight. At the same time, there are only four possible end groups and these can be dyed with fluorophores specific to the end groups. The above apparatus can identify the end group of the eluting fractions.

Certain oxidation-reduction reactions can be sensitively detected by chemiluminescence. The above apparatus can provide a good detector when an eluting sample triggers a chemiluminescence reaction.

Many more examples of the invention exist, each differing from the other in matters of detail only. The invention is to be determined solely by the appended claims.

I claim:

1. Apparatus for directing a radiation signal to a detector comprising means for generating an incident radiation signal caused by the interaction of a flowing sample with an exciting radiation source, reflection means being a reflecting surface of revolution having an axis and having a focal point, for receiving the generated incident radiation signal and for reflecting the incident signal as an output reflection signal to a detector, means for generating the incident radiation signal being substantially at the focal point of the reflection means, wherein at least one of the directions of the flowing sample or the direction of exciting radiation is substantially collinear with the axis of the reflecting surface at least at the focal point, means for flowing a sample substantially along the axis of revolution, said means being an elongated tube having a side wall, and wherein the exciting radiation source is a laser radiation such that the laser radiation essentially travels within the tube and is free of contacting the tube side wall.

2. Apparatus as claimed in claim 1 wherein the reflection means outputs a reflected collimated signal.

3. Apparatus as claimed in claim 1 wherein the reflection means outputs a reflected signal converging at a remote focus location.

4. Apparatus as claimed in claim 1 wherein the reflection means includes a parabolic surface.

5. Apparatus as claimed in claim 1 wherein the reflection means includes an ellipsoidal surface.

6. Apparatus as claimed in claim 1 including lens means between a reflection means and the detector.

7. Apparatus as claimed in claim 1 including filter means between the reflection means and the detector.

8. Apparatus as claimed in claim 1 including grating monochromater means between the reflection means and the detector.

9. Apparatus as claimed in claim 1 wherein the means for generating the incident light is at the focal point thereby permitting for a solid angle of incident light in the range between about 45° and about 135° relative to the axis of revolution.

10. Apparatus as claimed in claim 1 wherein the generated incident radiation signal selected from the group of a light scattered signal, Raman scattering fluorescence, phosphorescence, and luminescence signal, the incident radiation signal being generated by the impact of a laser radiation source directed on particles in the sample at the focal point.

11. Apparatus as claimed in claim 1 wherein the signal is selected from the group consisting of a light scattering signal, Raman scattering, fluorescence and phosphorescence and wherein the light beam laser radiation directed axially relative to the reflecting means and towards the focal point of the reflecting means, and wherein the sample flows axially substantially parallel with the laser radiation, and the axis of revolution.

12. Apparatus as claimed in claim 1 including focus means for the laser radiation wherein the focus means directs the radiation signal into contact with the sample at substantially the focal point.

13. Apparatus as claimed in claim 7 including an annular aperture between the reflection means and the detectors, the annular aperture being located in a plate spaced from the reflection means and wherein the center of the annular aperture is located on an axis of the reflection means.

14. Apparatus as claimed in claim 13 wherein the annular aperture has a predetermined diameter, the said diameter being determined in accordance with a predetermined incident radiation signal and a reflected signal from the reflection means.

15. Apparatus for directing a light scattered signal to a detector comprising reflecting means being a reflecting surface of revolution for receiving an incident light scattered signal, a focal point for the reflecting surface, a detector spaced from the reflecting surface, the reflecting means being for reflecting the light scattered signal to the detector, means for generating a laser radiation beam along an axis of the reflecting surface, means for directing a sample coaxially with the reflecting surface, such that the laser radiation beam and the sample impact at least at the focal point, means for directing the light scattered signal from the focal point of the reflecting surface such that the incident light scattered signal is directed from the reflecting surface towards the detector.

16. Apparatus as claimed in claim 15 including a tube axially directed relative tot he reflecting surface, the tube being directed to receive the laser radiation beam axially and to permit flow of the sample axially through the tube, and means optically occluding the tube selectively around its perimeter and permitting the incident point light scattered signal to exit from the tube at the focal point.

17. Apparatus as claimed in claim 16 including a cap on a downstream end of the tube optically occluding a light scattered signal, and a window on an upstream side of the tube, the window being optically isolated from the tube.

18. Apparatus for directing a radiation signal to a detector comprising reflection means being a reflecting surface of revolution having an axis and a focal point for receiving an incident radiation signal, a detector spaced from the reflecting surface, the reflecting means being for reflecting the incident radiation signal as a reflection signal to the detector, means for generating an excitation signal beam, a tube for flowing a sample, means for directing the excitation signal beam to impact a sample flow along the axis of radiation means at the focal point thereby generating the incident radiation signal substantially at the focal point such that the incident radiation signal is directed from the focal point over a solid angle in the range of about 45° to 135° relative to the axis of revolution, and optical occlusion means for optically occluding the tube from generating the incident radiation, the occlusion means about the tube defining barrier means, the barrier means radiating relative to the focal point to define the solid angle.

19. Apparatus as claimed in claim 18 wherein an excitation beam source is located adjacent the reflecting means, and including filter means downstream the reflecting means, the reflecting means generating a reflected signal from the incident signal generated at the focal point, the filtration means being for removing an excitation signal and for permitting passage of the reflected signal.

20. Apparatus as claimed in claim 19 including lens means downstream the filter means, the lens means focusing a reflected fluorescence signal on the detector.

21. Apparatus as claimed in claim 20 including a monochromator located between the reflecting surface and the detector, and including a diffraction mirror between the monochromator and the detector, the diffraction mirror focusing the reflected signal on the detector.

22. Apparatus for directing a radiation signal to a detector comprising a substantially curvilinear reflecting surface having a focal point and an axis of revolution, a detector, means for generating an incident radiation signal along the axis of revolution by the interaction of a sample with an excitation signal at the focal point, the sample being directed along the axis of revolution, means for directing the generated incident radiation signal to the reflecting surface, the reflecting surface reflecting an output signal to the detector, and including means for responding selectively to a spatial or temporal sorted signal, a Raman scatter signal.

23. Apparatus for directing a radiation light scattered signal to a detector comprising a curvilinear reflecting surface having a focal point and an axis of revolution, the reflecting surface being for receiving a generated incident radiation signal, means for directing a flowing sample axially relative to the axis of revolution towards the focal point, a detector, the reflecting surface transmitting a reflected signal to the detector, means for generating an incident radiation signal by the interaction of a sample with an excitation signal directed axially relative to the axis of revolution, including means for selecting the excitation radiation signal to have a wavelength greater than a particle size in the sample whereby the incident radiation reflected from the particles is isotropic.

24. Apparatus as claimed in claim 23 wherein the incident radiation signal disperses radiation over a solid angle range selected between about 45° and about 135° relative to the axis of the reflecting surface.

25. A method for directing a radiation signal to a detector comprising generating an incident radiation signal by the interaction of a sample with an excitation source, the sample and radiation from the excitation source being directed coaxially relative reflection means being a curvilinear reflecting surface of revolution source, receiving the generated incident radiation signal from a focal point of the reflecting surface, generating an output reflected signal from the reflecting surface, and directing the reflected signal to a detector.

26. A method as claimed in claim 25 wherein the reflected output signal is a collimated signal.

27. A method as claimed in claim 25 wherein the reflected output signal converges to a remote focus location.

28. A method as claimed in claim 25 wherein the generated radiation defines a solid angle in the range of about 45° to 135° relative to the axis of revolution.

29. A method as claimed in claim 25 wherein the curvilinear means selectively includes an ellipsoidal or parabolic surface.

30. A method as claimed in claim 25 including directing an excitation source axially relative to the reflection means.

31. A method as claimed in claim 25 wherein the radiation signal has a wavelength greater than a particle size in the sample such that the radiation reflected from the particles is isotropic.

32. A method as claimed in claim 25 wherein the signal from the sample reflects radiation over a solid angle range selected between about 45° and about 135° relative to the axis of the surface of revolution.

33. A method for directing a light scattered signal to a detector comprising generating a laser radiation beam along an axis of a curvilinear reflecting surface having a focal point, directing a sample axially to the focal point whereby the laser radiation beam impacts the sample at the focal point, and directing a light scattered generated signal from an impact at the focal point to the curvilinear reflecting surface and reflecting the incident light scattered signal towards a detector.

34. A method for directing a radiation signal to a detector, the signal being selected from the group consisting of a light scattered signal, Raman scattering, luminescence, phosphorescence and fluorescent signal, comprising generating an excitation signal beam and directing the excitation signal beam to a sample to generate an incident radiation signal, receiving a radiation signal on a curvilinear reflecting surface, the curvilinear surface having an axis of revolution and a focal point and being for reflecting the incident radiation signal from the focal point towards a detector, the sample and the excitation signal being coaxially directed relative to the axis of revolution and being directed towards each other at the focal point at a selected angle relative to each other, and wherein the generated radiation signal from the impact is generated at the focal point such that a generated radiation signal is directed to the curvilinear surface and in turn, towards the detector.

35. A method for directing a radiation signal to a detector comprising generating the radiation signal by the interaction of a sample with an excitation signal at a focal point of curvilinear reflecting means, the radiation signal and flow of the sample being coaxial, directing the generated signal as an incident radiation signal to the reflecting means, reflecting the incident signal to a detector and including having the detector respond selectively to a spatially or temporally sorted reflected signal.

36. Apparatus for directing a radiation signal to a detector comprising means for generating an incident radiation signal caused by the interaction of a flowing sample with an exciting radiation source, reflection means being a reflecting surface of revolution having an axis and having a focal point, and being for receiving the generated incident radiation signal and for reflecting the incident signal as an output reflection signal to a detector, and the means for generating the incident signal being at substantially the focal point, and means for flowing a sample wherein the flowing sample and the exciting radiation source are directed in a substantially collinear direction.

37. Apparatus as claimed in claim 36 including an elongated tube for the sample flow substantially along the axis of revolution, and wherein the tube includes a side wall, wherein the light beam is laser radiation, and including focus means for the laser radiation such that the radiation essentially travels within the tube and is free of contacting the tube side wall, an the focus means directs the radiation signal into contact with the sample at substantially the focal point.

38. Apparatus as claimed in claim 37 including a tube axially directed relative to the reflecting surface, the tube being directed to receive the laser radiation beam axially and to permit flow of the sample axially through the tube, and means optically occluding the tube selectively around its perimeter and permitting the incident point light scattered signal to exit from the tube at the focal point.

39. Apparatus as claimed in claim 38 including a cap on a downstream end of the tube optically occluding a light scattered signal, and a window on an upstream side of the tube, the window being optically isolated from the tube.

40. Apparatus for directing a light scattered signal to a detector comprising reflecting means being a reflecting surface of revolution for receiving an incident light scattered signal, the reflecting surface having a focal point, a detector spaced from the reflecting surface, the reflecting means being for reflecting the light scattered signal to the detector, means for generating a laser radiation beam, means for directing a sample into the area of the reflecting surface such that the laser radiation beam and the sample impact at least at the focal point, means for directing the light scattered signal from the focal point of the reflecting surface such that the incident light scattered signal is directed from the reflecting surface towards the detector, and wherein the means for directing the sample includes an elongated tube and wherein the laser radiation enters the sample through a window upstream of the tube, and the sample travels along a coaxial path upstream of a mouth to the elongated tube such that only laser radiation substantially axially directed and free of light scattered by the window when the laser radiation enters the sample flow passes through the tube.

41. Apparatus as claimed in claim 40 including a cap on a downstream end of the tube optically occluding a light scattered signal, and the window on the upstream side of the tube, the window being optically isolated from the tube.

42. Apparatus for directing a radiation signal to a detector comprising reflecting means for receiving an incident radiation signal, the reflecting means being a reflecting surface of revolution having an axis and a focal point, a detector spaced from the reflecting surface, the reflecting surface being for reflecting the incident radiation signal to the detector, means for generating an excitation signal beam, means for directing a sample flow coaxial with the axis, means for directing an excitation beam to impact the sample flow along the axis at the focal point thereby generating the incident radiation signal substantially at the focal point of the reflecting surface such that the incident radiation signal is directed from the focal point over a solid angle in the range of about 45° to 135° relative to the axis.

43. A method for directing a radiation signal to a detector comprising generating an incident radiation signal by the interaction of a sample with radiation from the excitation source, the sample and radiation from the excitation source being directed coaxially, receiving the generated incident radiation signal from a focal point of a reflecting surface, generating an output reflected signal from the reflecting surface, and directing the reflected signal to a detector.

44. A method as claimed in 43 wherein the generated radiation defines a solid angle in the range of about 45° to 135° relative to the axis of revolution.

45. A method as claimed in claim 43 wherein the reflecting surface selectively includes an ellipsoidal or parabolic surface.

46. A method as claimed in claim 43 wherein the radiation signal has a wavelength greater than a particle size in the sample such that the radiation reflected from the particles is isotropic.

47. A method as claimed in claim 43 wherein the signal from the sample reflects radiation over a solid angle range selected between about 45° and about 135° relative to the axis of the surface of revolution.

48. A method for directing a light scattered signal to a detector comprising generating a laser radiation beam to a focal point of a curvilinear reflecting surface, directing a sample axially to the focal point of the curvilinear reflecting surface along an axis of the curvilinear surface whereby the laser radiation beam impacts the sample at the focal point, directing a light scattered generated signal from an impact at the focal point to the curvilinear reflecting surface, and reflecting the incident light scattered signal towards a detector.

49. A method for directing a radiation signal to a detector, the signal being selected from the group consisting of a light scattered signal, Raman scattering, luminescence, phosphorescence and fluorescent signal, comprising generating an excitation signal beam and directing the excitation signal beam to a flowing sample to generate an incident radiation signal, receiving a radiation signal on a curvilinear reflecting surface, the curvilinear surface having an axis of revolution and a focal point and being for reflecting the incident radiation signal from the focal point towards a detector, the sample flow and the excitation signal being coaxial and being directed towards each other at the focal point at a selected angle relative to each other, and wherein the generated radiation signal from the impact is generated at the focal point such that a generated radiation signal is directed to the curvilinear surface and in turn, towards the detector.

50. A method for directing a radiation signal to a detector comprising generating the radiation signal by the interaction of a flowing sample with an excitation signal directed coaxially with the sample, the radiation signal being generated at a focal point of a curvilinear reflecting surface, directing the generated signal as an incident radiation signal to the reflecting surface, reflecting the incident signal to a detector, and including having the detector respond selectively to a spatially or temporally sorted reflected signal.

51. Apparatus for directing a light scattered signal to a detector comprising reflection means being a reflecting surface of revolution for receiving an incident light scattered signal, the reflecting surface having a focal point, a detector spaced from the reflecting surface, means for generating a laser radiation beam, means for directing a sample into the area of the reflecting surface such that the laser radiation beam and the sample impact at least at the focal point, means for directing the light scattered signal form the focal point of the reflecting surface such that the incident light scattered signal is directed from the reflecting surface towards the detector, and wherein the means for directing the sample includes an elongated tube and wherein the laser radiation enters the sample through a window upstream of the tube, and the sample travels along a coaxial path upstream of a mouth to the elongated tube such that only laser radiation substantially axially directed and free of light scattered by the window when the laser radiation enters the sample flow passes through the tube.

52. Apparatus for directing a radiation signal to a detector, the signal being caused by an interaction of a sample flow with an exciting radiation source, the apparatus comprising reflection means being a reflecting surface of revolution having an axis and having a focal point, and being for receiving a generated incident radiation signal and for reflecting the incident signal as an output reflection signal to a detector, the means for generating the incident radiation signal being substantially at the focal point, an elongated tube for a sample flow, the tube having a direction, such direction of the tube being substantially along the axis, and the exciting radiation source having a direction, such exciting radiation source direction being substantially collinear with the axis at least at the focal point.

* * * * *